US008311962B2

(12) United States Patent
Kato et al.

(10) Patent No.: US 8,311,962 B2
(45) Date of Patent: Nov. 13, 2012

(54) METHOD AND APPARATUS THAT DIVIDES, CLUSTERS, CLASSIFIES, AND ANALYZES IMAGES OF LESIONS USING HISTOGRAMS AND CORRELATION COEFFICIENTS

(75) Inventors: Noriji Kato, Kanagawa (JP); Takashi Isozaki, Tokyo (JP); Motofumi Fukui, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 597 days.

(21) Appl. No.: 12/557,137

(22) Filed: Sep. 10, 2009

(65) Prior Publication Data

US 2010/0076921 A1    Mar. 25, 2010

(30) Foreign Application Priority Data

Sep. 24, 2008 (JP) .................................. 2008-244253

(51) Int. Cl.
*G06E 1/00* (2006.01)
(52) U.S. Cl. ......................................................... 706/20
(58) Field of Classification Search .................... 706/12, 706/45, 20
See application file for complete search history.

(56) References Cited

U.S. PATENT DOCUMENTS

| 7,508,961 B2 * | 3/2009 | Chen et al. ..................... 382/118 |
| 2004/0206913 A1 * | 10/2004 | Costa et al. ................. 250/458.1 |
| 2006/0147094 A1 * | 7/2006 | Yoo ................................. 382/117 |
| 2007/0026363 A1 * | 2/2007 | Lehmann et al. ............. 433/223 |
| 2007/0217676 A1 * | 9/2007 | Grauman et al. ............. 382/170 |

OTHER PUBLICATIONS

Chi-Ren Shyu, et al.; "ASSERT: A Physician-in-the-Loop Content-Based Retrieval System for HRCT Image Databases"; Computer Vision and Image Understanding; 1999; pp. 111-132; vol. 75, No. 1.
Jennifer G. Dy, et al.; "Unsupervised Feature Selection Applied to Content-Based Retrieval of Lung Images"; IEEE Transactions on Pattern Analysis and Machine Intelligence; Mar. 2003; pp. 373-378; vol. 25, No. 3.
J. G. Dy, et al.; "The Customized-Queries Approach to CBIR Using EM"; IEEE Conference on Computer Vision and Pattern Recognition; 1999; pp. 400-406; vol. 2.
David M. Blei, et al.; "Latent Dirichlet Allocation"; Journal of Machine Learning Research 3; 2003; pp. 993-1022.

* cited by examiner

*Primary Examiner* — David Vincent
(74) *Attorney, Agent, or Firm* — Sughrue Mion, PLLC

(57) ABSTRACT

There is provided a similar image providing device including: a lesion region extracting unit that extracts a lesion region from a subject diagnostic image; a local image feature extracting unit that extracts local image features; a quantizing unit that quantizes the local image features; a lesion classifying unit that classifies a lesion; a storing unit storing correlation coefficients between local image features and topic variables expressing degrees of progression or degrees of seriousness of lesions; an expected value estimating unit that acquires expected values of probabilities of occurrence of topic variables; an image storing unit that stores diagnostic images and the expected values; and a providing unit that provides diagnostic images corresponding to expected values of topic probabilities of occurrence that best approximate the expected values of the topic probabilities of occurrence.

7 Claims, 4 Drawing Sheets

FIG. 2

|  | LOCAL IMAGE FEATURE | TOPIC VARIABLE A | TOPIC VARIABLE B | TOPIC VARIABLE C |
|---|---|---|---|---|
| LESION 1 | 1 | 0.12 | 0.70 | 0.05 |
|  | 2 | 0.75 | | |
|  | 3···. | 0.03 | | |
| LESION 2 | 1 | 0.32 | | |
|  | 2 | 0.01 | | |
|  | 3···. | 0.25 | | |

TOPIC PROBABILITIES OF OCCURRENCE

LESION REGION

FIG. 4
| DIAGNOSTIC IMAGE | EXPECTED VALUES | REPORT DATA |
|---|---|---|
| DIAGNOSTIC IMAGE 1 | (1, 0, 0) | ⋮ |
| DIAGNOSTIC IMAGE 2 | (0, 1, 0) | ⋮ |
| DIAGNOSTIC IMAGE 3 | (0.2, 0.3, 0.5) | ⋮ |
| DIAGNOSTIC IMAGE 4 | (0, 0, 1) | ⋮ |
| ⋮ | ⋮ | |
FIG. 5
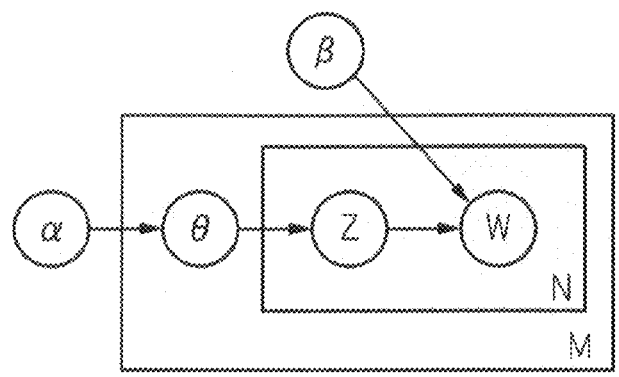
FIG. 6
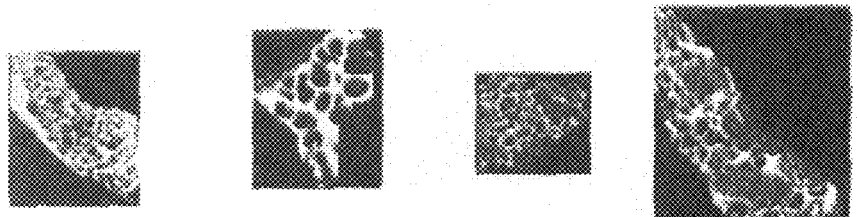
TOPIC
PROBABILITIES  (1, 0, 0)   (0, 1, 0)   (0, 0, 1)   (0.2, 0.3, 0.5)

METHOD AND APPARATUS THAT DIVIDES, CLUSTERS, CLASSIFIES, AND ANALYZES IMAGES OF LESIONS USING HISTOGRAMS AND CORRELATION COEFFICIENTS

CROSS-REFERENCE TO RELATED APPLICATION

This application is based on and claims priority under 35 USC 119 from Japanese Patent Application No. 2008-244253 filed on Sep. 24, 2008.

BACKGROUND

1. Technical Field

The present invention relates to a similar image providing device, method and program storage medium.

2. Description of the Related Art

In recent years, due to the spread of CT (Computed Tomography) and MRI (Magnetic Resonance Imaging) medical devices, digitalized diagnostic images can be acquired easily. Further, in hospitals, the large amount of diagnostic images that are acquired daily are filed electronically and can be stored easily, and diagnostic images can be used in common by plural doctors.

Usually, an image reading report, that expresses an opinion on an image and results of diagnosis that are obtained from reading the image, is attached to the diagnostic image. Therefore, these diagnostic images can be used as a database of a large number of cases. Thus, attempts have been made to make this large amount of accumulated cases useful for medical diagnoses. As one example, an attempt has been made to increase the accuracy of diagnosis by retrieving cases that are appended to images that are similar to an image to be diagnosed and referring to the results of the diagnoses that are written in the retrieved cases.

SUMMARY

In accordance with an aspect of the present invention, there is provided a similar image providing device including: a lesion region extracting unit that extracts a lesion region from a subject diagnostic image; a local image feature extracting unit that divides the lesion region into local images, and extracts local image features that characterize the respective local images; a quantizing unit that quantizes the local image features extracted by the local image feature extracting unit, and outputs quantized data; a lesion classifying unit that, on the basis of the quantized data outputted from the quantizing unit, classifies a lesion; a storing unit storing, per type of lesion, correlation coefficients between local image features and topic variables expressing degrees of progression or degrees of seriousness of lesions; an expected value estimating unit that acquires, from the storing unit, correlation coefficients between topic variables and respective local image features that are of the lesion classified by the lesion classifying unit and that are extracted by the local image feature extracting unit, and, by using the acquired correlation coefficients, estimates expected values of probabilities of occurrence of topic variables that generated the local features within the lesion; an image storing unit that stores, in association, diagnostic images and expected values of topic probabilities of occurrence that are computed in advance for the diagnostic images; and a providing unit that provides, as similar images and from among the diagnostic images stored in the image storing unit, diagnostic images corresponding to expected values of topic probabilities of occurrence that best approximate the expected values of the topic probabilities of occurrence that are estimated by the expected value estimating unit.

BRIEF DESCRIPTION OF THE DRAWINGS

An exemplary embodiment of the present invention will be described in detail based on the following figures, wherein:

FIG. 2 is a drawing showing the internal structure of a local image feature—topic variable correlation storing section 16;

FIG. 4 is a drawing showing the structure of an image storing section;

FIG. 5 is a drawing for explaining an LDA model; and

FIG. 6 is a drawing showing an example of providing diagnostic images corresponding to expected values of probabilities of occurrence of a topic.

DETAILED DESCRIPTION (Structure)

Figure 1:
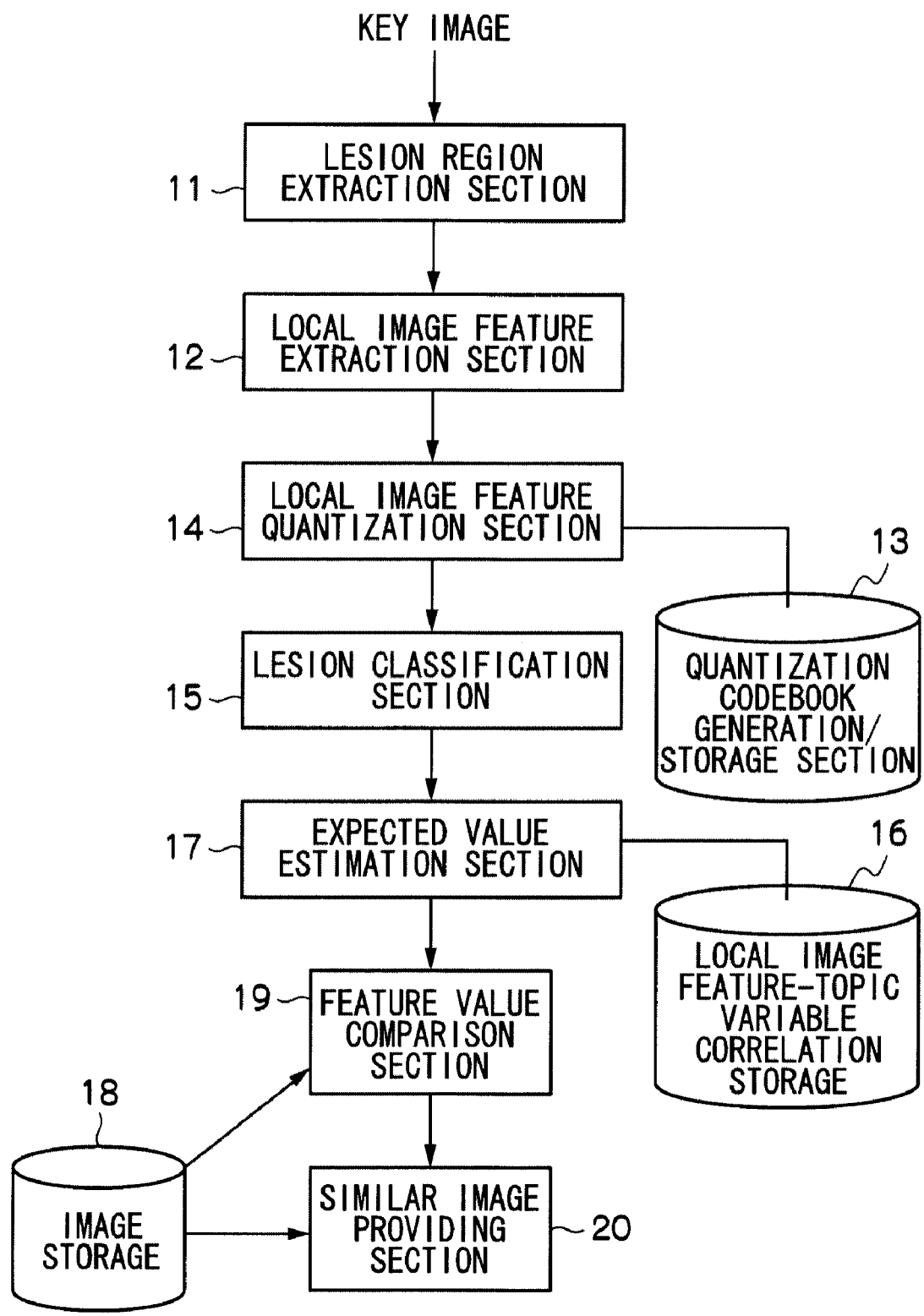
FIG. 1 is a block diagram showing the structure of a similar image providing device relating to the exemplary embodiment.

FIG. 1 is a block diagram showing the structure of a similar image providing device relating to an exemplary embodiment. The similar image providing device uses a case image provided by a user as a key image for searching, and searches for and provides past case images that are similar to the key image.

The similar image providing device includes a lesion region extracting section 11, a local image feature extracting section 12, a quantizing codebook generating/storing section 13, and a local image feature quantizing section 14. The lesion region extracting section 11 extracts a lesion region from the key image. The local image feature extracting section 12 extracts image features of local images. The quantizing codebook generating/storing section 13 prepares and stores a quantizing codebook. The local image feature quantizing section 14 quantizes local image features.

Further, the similar image providing device includes a lesion classifying section 15, a local image features—topic variable correlation storing section 16, and an expected value estimating section 17. The lesion classifying section 15 classifies lesions. The local image feature—topic variable correlation storing section 16 stores correlation coefficients between local image features and topic variables. The expected value estimating section 17 estimates expected values of probabilities of occurrence of topic variables that generate local features within lesions.

The similar image providing device further has an image storing section 18, a feature value comparing section 19, and a similar image providing section 20. The image storing section 18 stores, together with images, report data and expected values of probabilities of occurrence of topic variables. The feature value comparing section 19 compares feature values. The similar image providing section 20 provides similar images that have been retrieved.

Here, the local image feature—topic variable correlation storing section 16 stores correlations between topic variables and local image features that are learned in advance per type of lesion. A topic variable expresses the subclass, in a lesion of one type, that is the degree of progression or the degree of seriousness thereof.

FIG. 2 is a drawing showing the internal structure of the local image feature—topic variable correlation storing section 16. In the present exemplary embodiment, three topic variables A, B, C that correspond respectively to the speed of progression of the disease are used. As shown in FIG. 2, correlation coefficients between plural local image features and each topic variable are stored per lesion. The local image features and the topic variables are associated by learning plural lesion images in advance as will be described later.

Here, the topic variable expresses the subclass as mentioned above, but attaching labels to degrees of progression, degrees of seriousness or the like is difficult. Thus, the subclasses are acquired not by supervised learning, but by unsupervised learning. Further, in the present exemplary embodiment, the following generating model is considered in order to learn subclasses from feature values of lesion regions.

Figure 3:
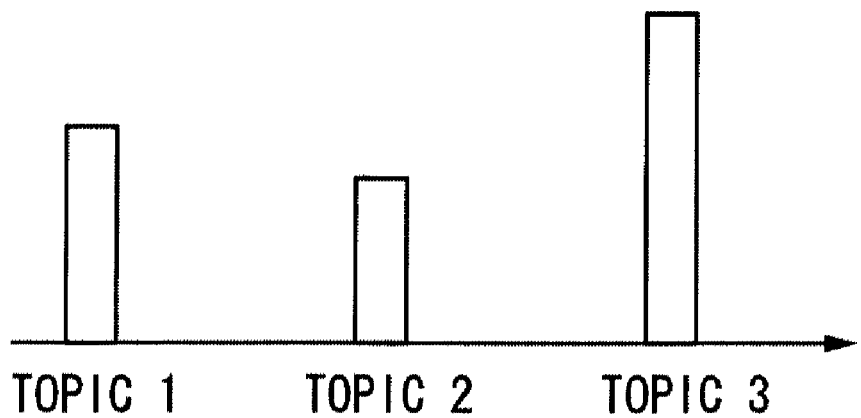
FIG. 3 is a schematic drawing showing a generating model in accordance with topic variables.
Figure 3:
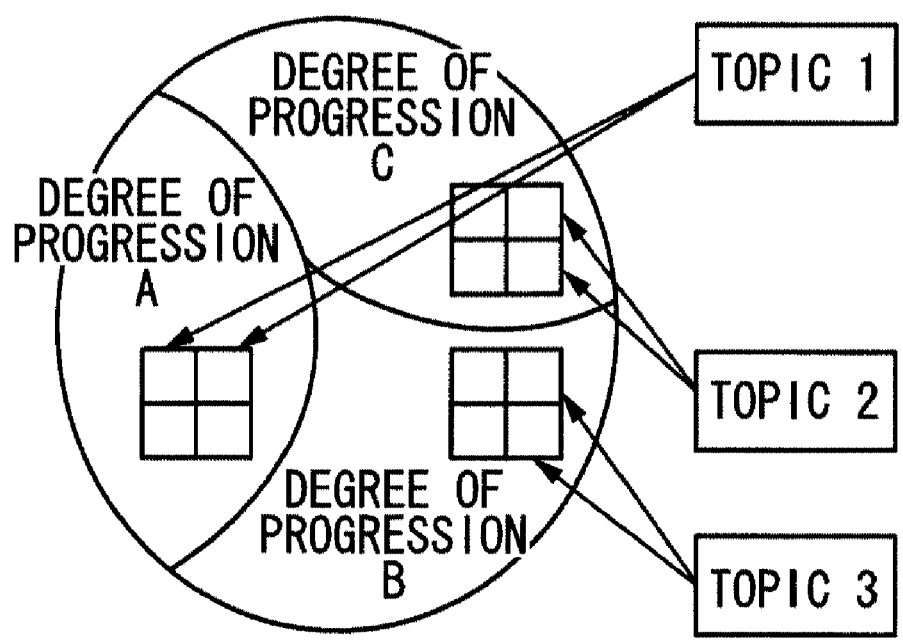

FIG. 3 is a schematic diagram showing a generating model in accordance with topic variables. In this example, there exist three topics A, B, C corresponding to degrees of progression of a disease. Probabilities that the respective topic variables will occur are provided for a lesion region as probabilities $P_A$, $P_B$, $P_C$, respectively. The topic variables occur with respect to the respective local regions in accordance with these probabilities.

Each topic variable generates a specific local feature at a given probability for that local region. For example, in FIG. 3, if the topic variable that occurred is A, there is a high probability that the local feature of the degree of progression A will arise. Note that the probability of a topic variable generating a local feature is determined by learning by providing lesion images. This learning will be described later.

Diagnostic images, expected values of topic occurrence probabilities, and report data are stored in the image storing section 18.

FIG. 4 is a drawing showing the structure of the image storing section 18. Diagnostic images that were taken in the past (if there is a lesion, the region thereof), expected values of topic occurrence probabilities that are computed in advance for the diagnostic images, and report data for the diagnostic images are stored in the image storing section 18.

The diagnostic images are, for example, files in the DICOM (Digital Imaging and Communication in Medicine) format that is the reference standard for medical imaging and communication. Information such as the patient ID, the examination date and time, and the like is stored in the header. The expected values of the topic occurrence probabilities are used for retrieving diagnostic images, and are computed in advance. The report data shows, for each diagnostic image, observations such as what diagnosis the doctor made and what kind of lesions existed and where they existed, and the disease name that was surmised as a result thereof.

(Learning)

The probability that a topic variable will generate a local feature is determined by learning by providing lesion images such as follows. The topic variable itself is a hidden variable that cannot be observed, but the expected value of the probability that a topic variable will occur with respect to a lesion image can be computed. In terms of FIG. 2, the expected values can be thought of as corresponding to the surface areas of the lesions A, B, C. Accordingly, by using the expected value of the probability of occurrence of a topic variable as a feature value of a lesion image, similar images can be retrieved even of lesions in which regions of differing degrees of progression or degrees of seriousness are mixed together.

A concrete form of a generating model is, for example, the Latent Dirichlet Allocation model (LDA model) in D. Blei, A. Ng, M. Jordan, "Latent Dirichlet Allocation", Journal of Machine Learning Research 3 (2003), pp. 993-1022.

FIG. 5 is a drawing for explaining the LDA model. Here, in the model, there are the parameter $\alpha$ of the Dirichlet distribution, and the probability $\beta$ of generating a local feature from each topic. $\alpha$ and $\beta$ are parameters that are computed by learning. Concretely, $\alpha$ expresses the Dirichlet distribution, and $\beta$ expresses probability P(Wi|topic j) that an ith word will appear from a jth topic.

The LDA model is widely used in statistical language processing. In the present invention a word W corresponds to a local image feature. Note that a number N of words W form one DOC, and learning is carried out by using a number M of the DOCs. Z is the topic variable. $\theta$ expresses at what probability a topic will occur in one DOC.

The probability of occurrence of each topic is assumed to be a polynomial distribution in which the Dirichlet distribution is a prior probability. For one lesion region, the probability of occurrence of each topic is determined, and, on the basis of the probability, a topic occurs for each local region, and a local feature is generated independently from that topic. These $\alpha$ and $\beta$ are learned by providing plural lesion regions. The likelihood for plural lesion regions can be defined by the following formula.

$$P(W|\alpha,\beta) = \frac{\Gamma\left(\sum_i \alpha_i\right)}{\prod_i \Gamma(\alpha_i)} \int \left(\prod_{i=1}^{k} \theta^{\alpha_i-1}\right)\left(\prod_{n=1}^{N}\prod_{i=1}^{k}\prod_{j=i}^{V} (\theta_i \beta_{ij})^{\delta_{nj}}\right)d\theta \quad \text{(Formula 1)}$$

Here, N expresses the number of regions that are obtained by the division by the local image feature extracting section 12. k is the number of topics, and, in the present exemplary embodiment, expresses the types (three types) of degrees of progression. V expresses the number of clusters of the k-means.

In the learning, the parameters $\alpha$ and $\beta$ are determined by making the likelihood that is defined by the above formula be a maximum. Methods such as the variational Bayes method and the Monte Carlo method are known as methods of maximizing. On the other hand, the expected values of the probabilities of occurrence of the respective topics for an inputted lesion image can be computed by using the learned parameters $\alpha$ and $\beta$. The computed expected values of the probabilities of occurrence are used as feature values of lesion regions.

(Similar Image Providing Processing)

When a key image, at which the current diagnosis is the lower layer, is inputted by a user as a search key, the similar image providing device that is structured as described above carries out processings as follows.

The lesion region extracting section 11 extracts a lesion region from the key image. The lesion region extracting section 11, for example, may make a region of a luminance of a predetermined range of the key image be a lesion region, or may compare the key image and a normal image without a lesion portion and extract, as a lesion region, a region at which the difference in the luminance is greater than or equal to a given value. Or, the user may designate the lesion region by a pointing device such as a mouse or the like.

The local image feature extracting section 12 divides the lesion region, that is extracted at the lesion region extracting section 11, into local regions of a uniform size, and computes image features for the images of the respective local regions (local images). Vector values whose components are the luminance values of the respective pixels of the local regions, edge features in which results of Sobel filtering that are computed at the respective pixels of the local regions are put into histograms within the regions, texture features using luminance level co-occurrence matrices, and the like are considered as image features.

The quantizing codebook generating/storing section 13 clusters sets of local image features within an unillustrated database by k-means clustering or the like, and stores the central value of each cluster. On the basis of a quantizing codebook that is stored in the quantizing codebook generating/storing section 13, the local image feature quantizing section 14 quantizes the local image features extracted at the local image feature extracting section 12. For example, the local image feature quantizing section 14 determines the cluster that is nearest to the local image feature, and outputs, as results of quantizing, the cluster number assigned to that cluster.

The lesion classifying section 15 computes a histogram of the local image features (cluster numbers) that are quantized by the local image feature quantizing section 14 within the lesion region, and classifies the lesion by using this histogram. The method of classifying lesions is not particularly limited, and the lesion classifying section 15 can classify lesions by using various classifying devices such as, for example, a support vector machine or the like. Therefore, it suffices for the lesion classifying section 15 to learn, in advance, lesion images and the diagnostic results thereof as teaching data.

In accordance with the results of classification at the lesion classifying section 15, the expected value estimating section 17 acquires the correlation coefficients between the local image features and the topic variables that are stored in the local image feature—topic variable correlation storing section 16. For example, if a lesion is classified as lesion 1 at the lesion classifying section 15, the expected value estimating section 17 acquires the local image feature for lesion 1 and the correlation coefficient of the topic variable corresponding thereto.

Next, by using the acquired correlations, the expected value estimating section 17 acquires the correlation coefficients between the topic variables and all of the local image features that are extracted at the local image feature extracting section 12, and, on the basis of the acquired correlation coefficients, estimates expected values of the probabilities of occurrence of the topic variables. For example, the expected value estimating section 17 determines the expected values by maximizing formula (1) with respect to the local features that are provided. Vectors, whose components are the estimated expected values of the probabilities of occurrence of the topics, are used as the feature values for searching.

The feature value comparing section 19 compares the expected values of the probabilities of occurrence of the topics estimated by the expected value estimating section 17 with respect to a lesion region within the key image, and the expected values of the probabilities of occurrence of the topics that are associated with the respective diagnostic images stored in the image storing section 18. Then, the feature value comparing section 19 selects, from among the expected values of the probabilities of occurrence of the topics stored in the image storing section 18, the expected values of the probabilities of occurrence of the topics that best approximate the estimated expected values of the probabilities of occurrence of the topics.

The similar image providing section 20 is structured by, for example, a display, and displays, as similar images and from among the diagnostic images stored in the image storage section 18, the diagnostic images associated with the expected values of the probabilities of occurrence of the topics selected at the feature value comparing section 19, and displays the opinions of the doctor and the disease names that are based on the report data that is associated with the diagnostic images as appendant information.

FIG. 6 is a drawing showing examples of providing diagnostic images corresponding to expected values of probabilities of occurrence of topics. As shown in FIG. 6, diagnostic images whose topic probabilities respectively correspond to (1,0,0), (0,1,0), (0,0,1) and (0.2,0.3,0.5) are provided by the similar image providing section 20.

Note that the present invention is not limited to the above-described exemplary embodiment, and can, of course, be applied to structures to which design changes have been made within the scope recited in the claims. For example, the expected values of the probabilities of occurrence of topics are not limited to the values determined from the above formula, and may be understood as being expected values of probabilities of forms that express respective topic variables.

What is claimed is:

1. A similar image providing device, comprising:
    a lesion region extracting unit that extracts a lesion region from a current diagnostic image by cropping the lesion region;
    a local image feature extracting unit that divides the lesion region of the current diagnostic image into local images of a uniform size, and extracts local image features that characterize the respective local images;
    a clustering unit that clusters sets of the local image features around respective central cluster values;
    a lesion classifying unit that computes a histogram showing the numbers of each cluster set around the respective central cluster value and the values of the local image features;
    a first storing unit that stores a plurality of stored diagnostic images, each stored diagnostic image having a diagnostic result that is determined in advance and a stored histogram computed in advance showing the stored cluster sets and the values of stored local image features of each stored diagnostic image;
    the lesion classifying unit compares the stored histograms of the stored diagnostic images with the computed histogram of the current diagnostic image, and classifies the lesion region according to the comparison;
    a second storing unit that stores stored correlation coefficients indicating probabilities of occurrence corresponding to stored topic variables and stored local image features, each stored topic variable expresses a degree of progression or a degree of seriousness of a specific lesion, the stored correlation coefficients are determined by using the stored diagnostic images;
    an expected value estimating unit that acquires current correlation coefficients for the current diagnostic image based on the local images features of the current diagnostic image and the stored correlation coefficients from the second storing unit, and estimates expected values of the probabilities of occurrence of the respective topic variables of the current diagnostic image by maximizing the probabilities of occurrence of the local image features;
    the first storing unit stores expected values of the probabilities of occurrence of the stored diagnostic image;
    a comparing section that compares the expected values of the probability of occurrences of the respective topic variables of the current diagnostic image with the expected values of the probability of occurrences of the respective topic variables of the stored diagnostic images, and selects one of the stored diagnostic images that best approximates the estimated expected values of the probability of occurrences of the respective topic variables of the current diagnostic image.

2. The similar image providing device as claimed in claim 1, wherein the topic variables are in a spectrum of low values to high values of the respective degrees of progression or degrees of seriousness, and the lesion region includes the plurality of topic variables.

3. The similar image providing device as claimed in claim 1, wherein the probabilities of occurrence of the respective topic variables of the current diagnostic image is a polynomial distribution in which a Dirichlet distribution is a prior probability.

4. The similar image providing device as claimed in claim 1, wherein the probabilities of occurrence corresponding to stored topic variables and stored local image features is a polynomial distribution in which a Dirichlet distribution is a prior probability.

5. The similar image providing device of claim 1, wherein
the first storing unit further stores, in association with the stored diagnostic images, diagnostic results data that express diagnostic results of the stored diagnostic images, and
the comparing section further provides, together with the stored diagnostic images, information that is based on the diagnostic results data corresponding to the stored diagnostic images.

6. A non-transitory computer readable storage medium storing a computer program causing a computer to execute a similar image providing method, comprising:
extracting a lesion region from a current diagnostic image by cropping the lesion region;
dividing the lesion region of the current diagnostic image into local images of a uniform size, and extracts local image features that characterize the respective local images;
clustering sets of the local image features around respective central cluster values;
computing a histogram showing the numbers of each cluster set around the respective central cluster value and the values of the local image features;
storing a plurality of stored diagnostic images, each stored diagnostic image having a diagnostic result that is determined in advance and a stored histogram computed in advance showing the stored cluster sets and the values of stored local image features of each stored diagnostic image;
comparing the stored histograms of the stored diagnostic images with the computed histogram of the current diagnostic image, and classifies the lesion region according to the comparison;
storing stored correlation coefficients indicating probabilities of occurrence corresponding to stored topic variables and stored local image features, each stored topic variable expresses a degree of progression or a degree of seriousness of a specific lesion, the stored correlation coefficients are determined by using the stored diagnostic images;
acquiring current correlation coefficients for the current diagnostic image based on the local images features of the current diagnostic image and the stored correlation coefficients from the second storing unit, and estimates expected values of the probabilities of occurrence of the respective topic variables of the current diagnostic image by maximizing the probabilities of occurrence of the local image features;
storing expected values of the probabilities of occurrence of the stored diagnostic image;
comparing the expected values of the probability of occurrences of the respective topic variables of the current diagnostic image with the expected values of the probability of occurrences of the respective topic variables of the stored diagnostic images, and selects one of the stored diagnostic images that best approximates the estimated expected values of the probability of occurrences of the respective topic variables of the current diagnostic image.

7. A similar image providing method, comprising:
extracting a lesion region from a current diagnostic image by cropping the lesion region;
dividing the lesion region of the current diagnostic image into local images of a uniform size, and extracts local image features that characterize the respective local images;
clustering sets of the local image features around respective central cluster values;
computing a histogram showing the numbers of each cluster set around the respective central cluster value and the values of the local image features;
storing a plurality of stored diagnostic images, each stored diagnostic image having a diagnostic result that is determined in advance and a stored histogram computed in advance showing the stored cluster sets and the values of stored local image features of each stored diagnostic image;
comparing the stored histograms of the stored diagnostic images with the computed histogram of the current diagnostic image, and classifies the lesion region according to the comparison;
storing stored correlation coefficients indicating probabilities of occurrence corresponding to stored topic variables and stored local image features, each stored topic variable expresses a degree of progression or a degree of seriousness of a specific lesion, the stored correlation coefficients are determined by using the stored diagnostic images;
acquiring current correlation coefficients for the current diagnostic image based on the local images features of the current diagnostic image and the stored correlation coefficients from the second storing unit, and estimates expected values of the probabilities of occurrence of the respective topic variables of the current diagnostic image by maximizing the probabilities of occurrence of the local image features;
storing expected values of the probabilities of occurrence of the stored diagnostic image;
comparing the expected values of the probability of occurrences of the respective topic variables of the current diagnostic image with the expected values of the probability of occurrences of the respective topic variables of the stored diagnostic images, and selects one of the stored diagnostic images that best approximates the estimated expected values of the probability of occurrences of the respective topic variables of the current diagnostic image.

* * * * *